US00PP09057P

United States Patent [19]

Fruehwirth

[11] Patent Number: Plant 9,057

[45] Date of Patent: Feb. 14, 1995

[54] POINSETTIA PLANT 'LATE BLOOMING FREEDOM'

[75] Inventor: Franz Fruehwirth, Encinitas, Calif.

[73] Assignee: Paul Ecke Ranch, Encinitas, Calif.

[21] Appl. No.: 192,440

[22] Filed: Feb. 7, 1994

[51] Int. Cl.[6] ..... A01H 5/00

[52] U.S. Cl. ..... Plt./86.4

[58] Field of Search ..... Plt. 86.4

*Primary Examiner*—James R. Feyrer

*Attorney, Agent, or Firm*—Arnold, White & Durkee

[57] ABSTRACT

Poinsettia 'Late Blooming Freedom' is a new cultivar, distinguished by dark red flower bracts, dark green foliage, naturally late flowering and self-branching characteristics. 'Late Blooming Freedom' is a sport of the poinsettia '490' (U.S. Plant Pat. No. 7,825) with the same cultural requirements. The new plant produces a very desirable late flowering branched pot plant.

1 Drawing Sheet

BACKGROUND OF THE NEW PLANT

This new poinsettia cultivar, 'Late Blooming Freedom', originated as a natural late flowering sport of poinsettia '490' (U.S. Plant Pat. No. 7,825) in my greenhouse in Encinitas, Calif. The new plant was observed as unique from among several thousand plants propagated from poinsettia '490' taken from a series of tip cuttings of the mature plant made over a period of several months beginning in March. It was selected because of its dark red flower bracts, dark green foliage, naturally late flowering, and self branching characteristics, traits which distinguish it from other poinsettia cultivars, and seem to make it a desirable plant for commercial greenhouse production. Under the same cultural and environmental conditions there were distinct differences between poinsettia 'Late Blooming Freedom' and poinsettia '490'. The plant height of 'Late Blooming Freedom' was taller. Its flower bracts at "full maturity" were smaller, more erect and more puckered than '490'. The bract color of 'Late Blooming Freedom' is dark red, and has more bluish tones. The color is not as bright as '490'. The greatest difference was that 'Late Blooming Freedom' flowered more than 2 weeks later than '490'. This offers certain economic advantages in that 'Late Blooming Freedom' was at optimum maturity for the late poinsettia market. After selection, 'Late Blooming Freedom' was vegetatively reproduced from stem cuttings for test purposes in Encinitas, Calif. Clones of the new sport were taken for 3–5 generations from tip cuttings of the mature plant. The distinctive characteristics of Late Blooming Freedom held true from generation to generation. The characteristics appeared to be genetically stable and not due to chemical treatment nor to microbial or viral infection of the plants.

DESCRIPTION OF THE PHOTOGRAPHS

Poinsettia 'Late Blooming Freedom' is illustrated in the accompanying color photographs. The upper photo is a side view of 3 single stem plants per pot in full flower. Evidence of self-branching can be seen in the flowering axillary branches beneath the upper canopy of bracts. The lower photo is a top view of the same plants showing flower and bract formation.

DESCRIPTION OF THE PLANT

The following chart shows some of the distinctive physical differences between Late Blooming Freedom and its parent '490'. Comparisons were made between plants grown under the same cultural conditions.

| | '490' | LATE BLOOMING FREEDOM |
|---|---|---|
| Bract Size | | |
| Length | 16–18 cm | 14–16 cm |
| Diameter | 30 cm | 28 cm |
| Height | 41 cm | 46 cm |
| Flower Res. time | 8 weeks | 10 weeks |
| Blooming Date (Northern Hemis) | November 15 | December 5 |
| Color | | |
| upper | 45A | 45A/B:46A/B |
| lower | 53C | 46B/C |

The following is a detailed description of this new poinsettia as observed in Encinitas, Calif., U.S.A. during December 1993. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Naturally occurring sport of Poinsettia '490' (U.S. Plant Pat. No. 7,825).

Classification:

*Botanic.*—*Euphorbia pulcherrima* Willd.

*Common name.*—Poinsettia.

*Cultivar name.*—'Late Blooming Freedom'.

Form: Shrub.

Height: Medium.

Growth habit: As a single stemmed plant, upright and vigorous with self-branching side shoots. The cultural requirements appear to be the sae as for the parent, poinsettia '490'. The application of a chemical growth retardant may be needed to restrict height for commercial pot plant production. I observed 3 unpinched plants in a pot with an overall height of 46 cm. and an overall width of 48 cm. The bract diameter of individual flowers was 28 cm. By contrast at "full flower," cultivar '490' had an overall height of 41 cm.

Branching: Axillary branches will develop and terminate in a flower without pinching. However, it is usually desirable to pinch 'Late Blooming Freedom' before flower induction and remove all terminal dominance. Then, all axillary branches will develop uniformly and at a faster rate.

Growth rate: Rooting of stem cutting occurs in 12–18 days under intermittent mist. The plant will flower in about ten weeks under continuous long night conditions and night temperatures of about 16–18 degrees C. In my greenhouse, poinsettia 'Late Blooming Freedom' reached full maturity on December 5. Its parent, poinsettia '490', was fully mature on November 15.

Foliage: The foliage is clean and uniformly dark green from bottom to top of the plant. The leaves are of medium size, leaf blades typically being 14–15 cm. long and 9–10 cm. wide with leaf petioles 4–5 cm. long.

*Leaf shape.*—Typical leaves are generally ovate with obtuse bases and acuminate tips. Leaf margins are mostly entire or occasionally slightly lobed with 1–2 indentations on each side of the leaf blade.

*Color.*—Upper side — Dark green, darker than RHS 147A. Under side — Green, between RHS 147A-B.

*Retention.*—The foliage lasts extremely well even under low light intensities in the consumer's home.

Bracts: Generally there are 18–21 dark red, somewhat puckery bracts of various sizes subtending the cyathia. The primary bracts are medium to large, have blades typically 14–16 cm. long and 10–11 cm. wide with petioles 3–4 cm. long. Secondary bracts are smaller and of various sizes with bract petioles 2–3 cm. long.

*Shape.*—Bracts are ovate with acute bases and acuminate tips. Primary bracts margins are entire. Secondary bracts are elliptic and have entire margins.

*Color.*—Upper side — Dark red, between RHS 45A-B and RHS 46A-B. Under side — Red, between RHS 46B-C.

Flowers: Generally, 18–21 cyathia (flowers) were present when the plant was in full bloom. Each cyathium is about 7 mm long and 5 mm wide, green in color, and fringed with red at the distal end. A yellow nectar cup protrudes from the side of each cyathium. The flower pedicel is also green and about 5 mm in length. The stamens protruding from the cyathia are red. The anthers are bifurcate; the pollen is yellow and copious. The stigmas are red and trifurcate.

*Nectar exudate.*—Present, abundant.

*Seed formation.*—Self-incompatible.

*Fertility.*—Not observed.

What is claimed is:

1. A new and distinct Poinsettia cultivar, substantially as herein shown and described, distinguished by its dark red flower bracts, dark green foliage, naturally late flowering and self branching traits.

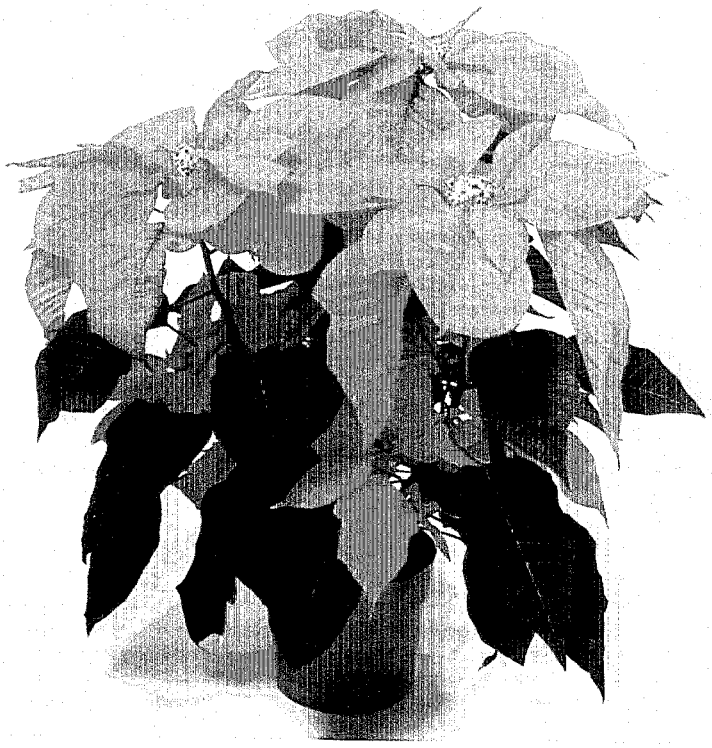
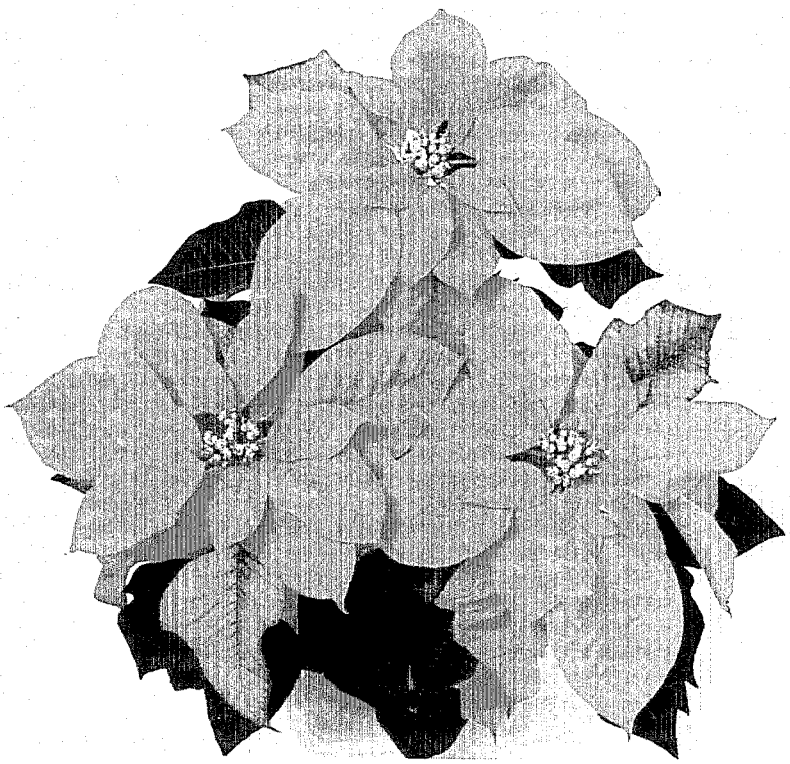

* * * * *